(12) United States Patent
Anziano

(10) Patent No.: US 6,737,506 B1
(45) Date of Patent: May 18, 2004

(54) MANGANESE SUPEROXIDE DISMUTASE EXON 3-DELETED ISOFORMS AND NUCLEIC ACID MOLECULES ENCODING THE ISOFORMS

(75) Inventor: Paul Q. Anziano, Philadelphia, PA (US)

(73) Assignee: Paul Anziano, Philadelphia, PA (US)

( * ) Notice: Subject to any disclaimer, the term of this patent is extended or adjusted under 35 U.S.C. 154(b) by 0 days.

(21) Appl. No.: 09/623,025

(22) PCT Filed: Feb. 25, 1999

(86) PCT No.: PCT/US99/04129

§ 371 (c)(1),
(2), (4) Date: Jan. 16, 2001

(87) PCT Pub. No.: WO99/43697

PCT Pub. Date: Sep. 2, 1999

Related U.S. Application Data

(60) Provisional application No. 60/075,948, filed on Feb. 25, 1998.

(51) Int. Cl.⁷ .................................................. C07K 7/00
(52) U.S. Cl. .......................... 530/300; 530/350; 435/86
(58) Field of Search ................................ 530/300, 350; 436/86

(56) References Cited

PUBLICATIONS

T. Hoey, *Introduction to Expression by Fusion Protein Vectors, Current Protocols in Molecular Biology*, University of California Berkeley, California.

Yibling Li, et al., *Dilated Cardiomyopathy and Neonatal Lethality in Mutant Mice Lacking Manganese Superoxide dismutase*, Nature Genetics, vol. 11, Dec. 1995.

Sari Pitkänen, et al., *Mitochondrial Complex I Deficiency Leads to Increased Production of Superoxide Radicals and Induction of Superoxide Dismutase*, Departments of Pediatrics and Biochemistry, University of Toronto, Ontario; and Department of Genetics, The Research Institute, The Hospital for Sick Children, Toronto, Ontario.

B. H. Robinson, *The Role of Manganese Superoxide Dismutase in Health and Disease*, J. Inher. Metab. Dis. 21 (1998) 598–603.

*Primary Examiner*—James Housel
*Assistant Examiner*—Myron G. Hill
(74) *Attorney, Agent, or Firm*—Morgan Lewis & Bockius LLP

(57) ABSTRACT

An isoform of manganese superoxide dismutase (MnSOD) and polynucleotides encoding it have been identified. This isoform, MnSOD E3(–), is a splice variant lacking exon 3 of the full length MnSOD. The polypeptide can be expressed using appropriate host cells. Modulation of either the expression of the polynucleotides or the activity of the polypeptide is also described. Furthermore, diagnostic and therapeutic methods have been developed as a consequence of the isolation of the polynucleotides and polypeptides.

11 Claims, 10 Drawing Sheets

MnSOD E2/E3/E4 →  ● ●●●●●●●●●●●  331 nt

MnSOD E2/E4  →   ●      -    ●     - 215 nt
```

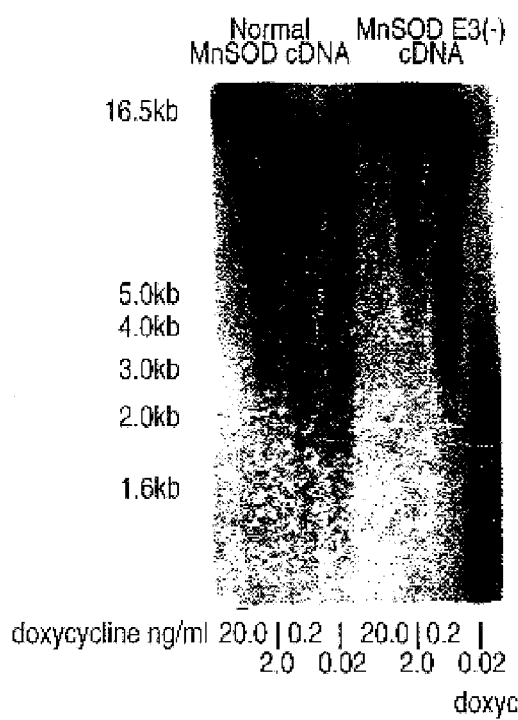
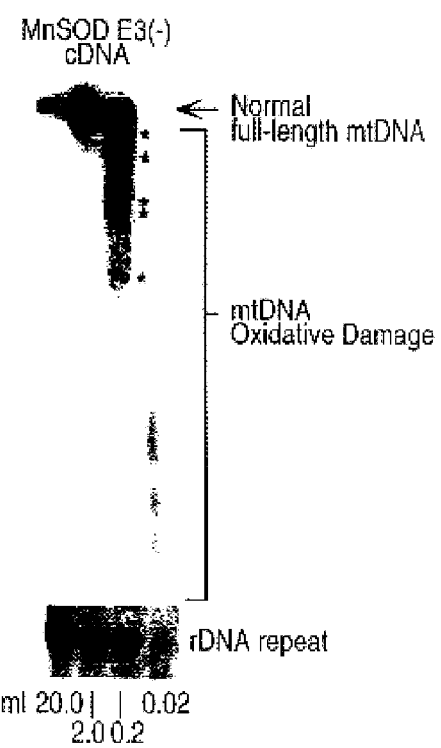
FIG. 5A
FIG. 5B

|  | 1 | 2 |
|---|---|---|
| MnSOD antibody |  | |
| MnSOD E3(-) isoform antibody |  | |

MANGANESE SUPEROXIDE DISMUTASE EXON 3-DELETED ISOFORMS AND NUCLEIC ACID MOLECULES ENCODING THE ISOFORMS

CROSS REFERENCE TO RELATED APPLICATIONS

This application is a national stange entry of PCT/US99/04129, filed Feb. 25, 1999, claims the benefit of U.S. Provisional Application Serial No. 60/075,948, filed Feb. 25, 1998, which is herein incorporated by reference in its entirety.

FIELD OF THE INVENTION

This invention is directed toward modulating oxidative damage to intracellular components such as mitochondrial DNA (mtDNA) and mitochondrial protein. More particularly, the invention is directed toward a newly identified isoform of manganese superoxide dismutase, related polynucleotides and polypeptides, and their production and uses.

BACKGROUND OF THE INVENTION

A. Superoxide Dismutase

Superoxide radicals and other highly reactive oxygen species are harmful by-products produced in every respiring cell, causing oxidative damage to a wide variety of macromolecules and cellular components. A group of metalloproteins known as superoxide dismutases (SOD) catalyzes the oxidation-reduction reaction $2O_2^- + 2H^+ \rightarrow H_2O_2 + O_2$ and thus provides a defense mechanism against oxygen toxicity. SOD may contain manganese or iron or a combination of copper and zinc (U.S. Pat. No. 5,540,911).

Oxidative damage has been positively correlated with a reduction in MnSOD activity (Isoherranen et al., *J Photobiol* (1997) 40(3):288–293); hence, SODs from various sources are currently of great interest as potential therapeutic treatments for oxidative damage. Their use in a clinical setting for the treatment of a wide variety of disorders has been proposed (see Beck et al., *Nuc Acids Res* (1988) 15(21): 9076). These proposals include (i) prevention of oncogenesis, tumor promotion and invasiveness, and UV-induced damage; (ii) protection of cardiac tissue against post-ischernia reperfusion damage; (iii) as an anti-inflammatory agent; (iv) to reduce the cytotoxic and cardiotoxic effects of anticancer drugs, and; (v) to improve the longevity of living cells (U.S. Pat. No. 5,772,996).

The importance of reactive oxygen species (ROS) or changes in the cellular redox state in the pathogenesis of viral infections is becoming increasingly evident. For example, influenza virus infection of the lungs induces MnSOD expression and thus is associated with oxidative stress (Choi et al., *Am J. Physiology* (1996) 271(3 Pt 1): L383–391). Further, SOD, specifically MnSOD, is recognized in the art to be modulated during various stages of viral infection (e.g., Choi et al Am J. Physiology (1996) 271(3 Pt. 1): L383–391; Ritter et al., J Exp Med (1994) 185(5): 1995–1998; Jacoby et al., *Free Radic Biol Med* (1994) 16(6): 821–824; and Carbonari et al., (1997) 90(1): 209–216). This is especially acute in HIV infections, wherein the effect of cytokines, such as TNF alpha, may further exacerbate the effects of oxidative stress in the infective pathogenesis associated with AIDS (Le Naour, et al., Res Immunol (1992) 143(1): 49–56 and Shatrov et al., *Eur Cytokine Network* (1997) 8(1): 37–43).

Patients infected with HIV-1 often display destroyed immune cells in the peripheral lymphoid tissues as well as exhibit cognitive defects that are related to progressive neuronal degeneration and cell death involving the redox state (New et al., Neurovirol (1997) 3(2): 168–173 and Flores et al., *Proc Natl Acad Sci USA* (1993) 90(16): 7632–7636). HIV-infected patients have also shown low levels of MnSOD (Zhang et al., *Antioxidants and AIDS*, 36–37 (CRC Press LLC, 1997). Apoptosis and aging involve oxidative stress as measured by degradation of mtDNA (Ozawa T., *Biosci Rep* (1997) 17(3):237–250). What is of critical relevance is that all of these events reflect the involvement of moderate to severe mitochondrial damage (e.g., mtDNA deletions) in part due to the effects of ROS (Kruman et al., Exp Neurol (1998) 154(2): 276–288; and Carbonari et al., (1997) 90(1): 209–216).

B. Mitochondrial Damage

To meet the body's acute and chronic energy demands, all cells of the body synthesize their fuel within their mitochondria. Mitochondrial DNA (mtDNA) contains thirteen genes encoding protein products that are necessary to synthesize the cell's fuel, adenosine triphosphate (ATP). All cells have mitochondria, but the number of mitochondria per cell can vary from a few hundred to tens of thousands per cell.

Mitochondrial oxidative stress has often been implicated as an initiator of the mtDNA mutation process because mitochondria consume most of the cell's oxygen for ATP synthesis. If oxygen is not metabolized efficiently, oxygen free radicals can accumulate in the cell. Free radicals can cause protein and lipid peroxidation, as well as oxidative damage to the mtDNA. If oxidative damage to mtDNA is left unrepaired, the point-mutation and deletion rate of the mtDNA increases, which may eventually lead to permanent organ fatigue.

A random mutation on one mtDNA molecule would not alone be deleterious to an organism due to the large intracellular pool of mtDNA. Accordingly, a few random mtDNA mutations may have no distinguishable phenotypic effects, but once a high level of these mtDNA mutations has accumulated in critical cells, an energy-loss syndrome may occur which could effect the heart (cardiomyopathy or conduction disorders), the brain (seizures, dementia), pancreas (non-insulin dependent diabetes), the gastrointestinal tract (dysmotility or pseudo-obstruction), inner ear (sensorineural hearing loss), kidney (glomerulopathy) and/or the skeletal muscle (myopathy).

As oxidative stress can induce both mtDNA mutations and apoptotic death, the discovery that mtDNA mutations are the basis of a number of human pathologies may have profound implications.

C. Cell Death

Programmed cell death (sometimes referred to as apoptosis) is distinguishable, both morphologically and functionally, from necrosis. Programmed cell death is a natural cellular event. Cells dying by programmed cell death usually shrink, rarely lyse, and are efficiently removed from the organism without the appearance of inflammation. Necrosis, however, is a pathological type of cell death observed following physical or chemical injury, exposure to toxins or ischemia (lack of oxygen). Dead cells are rapidly recognized and engulfed by macrophages (Michael Hengartner, Cell Death and Aging, Molecular Mechanisms of, *Molecular Biology and Biotechnology*, 158–62 (ed. R. A. Meyers, 1995)).

It is becoming increasingly clear that oxygen metabolism plays a key control point in programmed cell death or apoptosis. Therefore, identifying the gene product responsible for apoptotic oxidative stress is key to therapeutic drug development. In cancer, for example, it would be therapeutically advantageous to be able to induce apoptosis in malignant cells by increasing oxidative stress in these cells.

Conversely, inhibiting oxidative stress may prolong cell life. The immune activation of T cells of HIV-infected individuals leads to oxidative damage of proteins and lipids and apoptotic T cell death (Piedimonte et al. (1997) Infect Dis 176: 655–664; Walmsley et al. (1997) AIDS 11(14):1689–1697; Groux et al. (1992) J Exp Med 175: 331–340). Oxidative stress also causes HIV viral load to increase (Schreck et al. EMBO J (1991) 10 (8):2247–2258; Staal et al., *Proc Natl Acad Sci USA* (1990) 87: 9943–9947). Therefore, inhibiting oxidative stress might be beneficial in preventing T cell depletion in HIV-infected individuals.

Therefore, given the importance of the redox state on cell function and homeostasis, there is a need to identify any gene and/or gene product having a role in oxidative stress.

SUMMARY OF THE INVENTION

Applicants have identified a new isoform of MnSOD that is referred to herein as "MNSOD E3(−)" because it is a splice variant lacking exon 3 of the full length MNSOD. Unlike the antioxidant MnSOD, MnSOD E3(−) is believed to have a pro-oxidant effect within a cell.

In a first embodiment, the invention provides isolated nucleic acid molecules that are: (a) an isolated nucleic acid molecule that encodes the amino acid sequence of SEQ ID NO:2; (b) an isolated nucleic acid molecule that encodes an exon 3 deleted MnSOD; (c) an isolated nucleic acid molecule which comprises SEQ ID NO:1; (d) an isolated nucleic acid molecule that is the complement of (a), (b), or (c); (e) an isolated nucleic acid molecule that encodes an MnSOD and comprises the sequence TAC CAG GAG GCG TTG GCC AAG GGG GAG TTG CTG GAA GCC ATC AAA (SEQ ID NO:3); or (f) an isolated nucleic acid molecule that encodes an MnSOD comprising the amino acid sequence GlnGluAlaLeuAlaLysGlyGluLeu LeuGluAla (SEQ ID NO:4). These nucleic acid molecules can be used to produce novel vectors and novel host cells containing the vectors.

The invention also provides a polypeptide, particularly MnSOD E3(−), and a method of producing it by culturing a host cell transformed or transfected with the nucleic acid molecule described above under conditions in which the polypeptide encoded by the nucleic acid molecule is expressed.

The invention further provides methods of identifying agents that modulate the expression of a nucleic acid molecule encoding a polypeptide, preferably MnSOD E3(−), and agents that modulate at least one activity of the polypeptide itself. These methods include exposing cells which express either the nucleic acid molecule or the polypeptide to a potential agent and determining whether the agent modulates the expression of the nucleic acid or the activity of the polypeptide.

The identification of MnSOD E3(−) has led to the discovery of methods of diagnosing oxidative stress in a cell or tissue sample. As stated, oxidative stress leads to mtDNA and protein degradation. MnSOD E3(−) has also been observed in PMBCs from samples taken from patients whose immune system has been activated, for instance, by viral infection or vaccination. A first method includes exposing the cell or tissue sample to an agent, such as a nucleic acid probe, which specifically binds to the nucleic acid molecule described above. A diagnosis can then be made upon determining whether the agent has specifically bound to the cell or tissue sample. A second method includes exposing the cell or tissue sample to an agent, such as an antibody, which specifically binds to a polypeptide, preferably one containing the exon 2-exon 4 junction of MnSOD E3(−).

The invention also provides methods of promoting death or apoptosis of a cell. One method includes the step of modulating the level of the nucleic acid molecule described above. Another method includes the step of exposing a cell to an exon 3-deleted MnSOD polypeptide.

Additionally, the invention provides a method of inhibiting oxidative-dependent death or apoptosis of a cell. This method includes the step of modulating, particularly inhibiting, the level of expression of the nucleic acid molecule described above.

The accompanying figures, which are incorporated in and constitute a part of this specification, illustrate several embodiments of the invention. The figures and their descriptions serve to explain the principles of the invention.

BRIEF DESCRIPTION OF THE FIGURES

FIG. 2 shows RT/PCR products of recombinant cDNA MnSOD, recombinant cDNA MnSOD E3(−), normal heart cDNA MnSOD, normal WBC cDNA MnSOD, cDNA of WBC under oxidative stress, RNA of WBC during active or inactive production of Epstein-Barr virus, WBC cDNA of ALS patient, and lymphoblast cDNA.

FIG. 5 shows mtDNA oxidative damage following transient transfection of HEK293 tet-off cells with the full length MnSOD cDNA and with the MnSOD E3(−) cDNA.

DESCRIPTION OF THE INVENTION

Figure 1A:
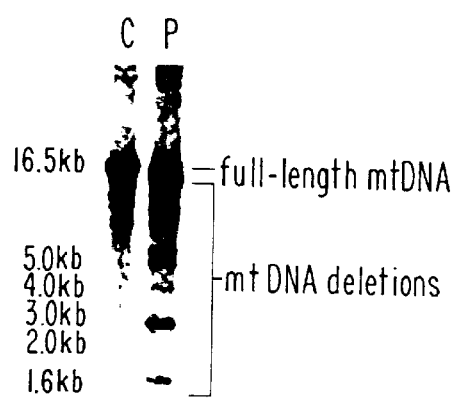
FIG. 1A shows a Southern hybridization gel using a full-length mtDNA P-32 probe against PMBC mt DNA of a healthy control and a patient with multiple mtDNA deletions.

One embodiment of the present invention comprises a nucleic acid molecule which is useful for monitoring the immune status of a patient.

An "exon 3 deleted MnSOD" molecule as used herein comprises no third exon relative to the antioxidant from of MnSOD. Further, an exon 3 deleted MnSOD lacks the active site histidine required for manganese binding as well as the peptide sequences required for forming the final homotetrameric complex of antioxidant-MnSOD associated with oxygen capture. In a related aspect, exon 3 deleted MnSOD relates to polynucleotides which encode polypeptides the are defined by the above mentioned structure/function parameters. Further, polynucleotides are envisaged which hybridize to the hereinabove described polynucleotide sequences if there is at least 50% and preferably 70% identity between the sequences. The present invention particularly relates to polynucleotides which hybridize under stringent conditions to the hereinabove described polynucleotides. As used herein, the term "stringent conditions" means hybridization will occur only if there is at least 95%, and preferably 97%, identity between the sequences and the sequences do not encode MnSOD containing exon 3.

In a preferred embodiment, the polynucleotides which hybridize to the hereinabove described polynucleotides encode polypeptides which retain substantially the same activity as an exon 3 deleted MnSOD. In a further aspect, specific stringency conditions are determined according to Sambrook et al., Molecular Cloning: A Laboratory Manual (2nd ed) (Ford et al. Eds) 1989, pages 1.74–1.84; 4.12, 4.37–4.38 and 16.30–16.55, Cold Spring Harbor Laboratory Press, Cold Spring Harbor, N.Y.

Homology or identity can be determined by BLAST (Basic Local Alignment Search Tool) analysis using the algorithm employed by the programs blastp, blastn, blastx, tblastn and tblastx (Karlin, et al. Proc. Natl. Acad. Sci. USA 87: 2264–2268 (1990) and Altschul, J. Mol. Evol. 36: 290–300(1993), fully incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (Nature Genetics 6: 119–129 (1994)) which is fully incorporated by reference. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff, et al. Proc. Natl. Acad. Sci. USA 89: 10915–10919 (1992), fully incorporated by reference). For blastn, the scoring matrix is set by the ratios of M (i.e., the reward score for a pair of matching residues) to N (i.e., the penalty score for mismatching residues), wherein the default values for M and N are 5 and −4, respectively.

In a preferred embodiment an exon 3-deleted MNSOD may include (i) a fragment, derivative or analog of the polypeptide as set forth in SEQ ID NO: 2, (ii) a polypeptide in which one or more of the amino acid residues are substituted with a conserved or non-conserved amino acid residue (preferably a conserved amino acid residue) while retaining at least 70% sequence identity with the polypeptide as set forth in SEQ ID NO: 2 wherein such substituted amino acid residues may or may not be amino acids encoded by the genetic code, (iii) a polypeptide in which one or more of the amino acid residues includes a substituent group, (iv) a polypeptide in which the mature polypeptide is fused with another compound to increase the half-life of the polypeptide (for example, polyethylene glycol) or (v) a polypeptide in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein, including that such fragments, derivatives and analogs maintain the substantially identical activity of the polypeptide set forth in SEQ ID NO: 2.

"Nucleic acid molecule" as used herein includes DNA and RNA molecules and is used synonymously with the terms "nucleic acid sequence" and "polynucleotide."

"Polypeptide" as used herein denotes an amino acid sequence including, but not limited to, proteins and protein fragments, naturally derived or synthetic.

"Mature polypeptide" as used herein refers to a gene product wherein all physiological posttranslational modifications have occurred prior to glycosylation. For example, for a mature polypeptide envisaged by the present invention, all prepro sequences present in the nascent form of the polypeptide are absent.

"Oxidative stress" as used herein refers to injury, damage, or trauma produced by attack of reactive oxygen species.

"Apoptosis" or "programmed cell death" is the natural elimination of cells that are no longer necessary, that are produced in excess, that have developed improperly or that have sustained genetic damage. In contrast, "necrosis" is a pathological type of cell death observed, for example, in ischemia following physical or chemical trauma.

"Exon" as used herein refers to DNA of the gene which that is represented in the mature RNA product. For example, "E1, E2, E3, E4 and E5" refer to exons 1–5 of the MnSOD structural gene.

"Intron" as used herein refers to DNA of the gene that is removed from the mature RNA product.

The "activity" of an exon 3-deleted MnSOD refers to an effect of the entity on its environment. This may include, for example, nonspecific mtDNA oxidative damage, inability to appropriately bind $Mn^{++}$ and/or inability to form the homotetrameric structure of antioxidant-MnSOD. In another example, the biological activity of an exon 3 deleted MnSOD could refer to the immunological specificity of an epitope comprising Gln-Glu-Ala-Leu-Ala-Lys-Gly-Glu-Leu-Leu-Glu-Ala (SEQ ID NO:4), wherein antibody recognition is directed to this epitope.

A nucleic acid molecule of the present invention was isolated from the peripheral mononuclear blood cells (PMBCs) of a human patient with mild anemia, mild leukopenia and multiple mtDNA deletions. It contains an open reading frame encoding a polypeptide of 222 amino acids. The polypeptide is identical to MnSOD except that the polypeptide lacks the third encoding exon (E3) of the MnSOD gene and is recognized as a splice variant of the full length form.

In accordance with an aspect of the present invention, there is provided an isolated nucleic acid molecule which encodes for the mature exon 3-deleted polypeptide having the deduced amino acid sequence as set forth in SEQ ID NO: 2.

The polynucleotide of the present invention may be in the form of RNA or in the form of DNA, which DNA includes cDNA, genomic DNA and synthetic DNA. The DNA may be double stranded or single stranded, and if single stranded, may be the coding strand or non-coding (antisense) strand. The coding sequence which encodes the mature exon 3-deleted polypeptide may be identical to the coding sequence as set forth in SEQ ID NO: 1. Alternatively, the coding sequence may be different from SEQ ID NO: 1 but encodes, because of degeneracy of the genetic code, the same mature exon 3-deleted polypeptide as the DNA as set forth in SEQ ID NO: 1.

The polynucleotide which encodes for the mature exon 3-deleted polypeptide as set forth in SEQ ID NO: 2 may include 1) only the coding sequence for the polypeptide or 2) the coding sequence for the polypeptide and additional coding sequences such as a leader, a signal or a proprotein sequence. A preferred polynucleotide is represented as follows:

ATG TTG AGC CGG GCA GTG TGC GGC ACC AGC AGG CAG CTG CCT CCG GTT TTG GGG TAT CTG GGC TCC AGG CAG AAG CAC AGC CTC CCC GAC CTG CCC TAC GAC TAC GGC GCC CTG GAA CCT CAC ATC AAC GCG CAG ATC ATG CAG CTG CAC CAC AGC AAG CAC CAC GCG GCC TAC GTG AAC AAC CTG AAC GTC ACC GAC GAG AAG TAC CAG GAG GCG TTG GCC AAG GGG GAG TTG CTG GAA GCC ATC AAA CGT GAC TTT GGT TCC TTT GAC AAG TTT AAG GAG AAG CTG ACG GCT GCA TCT GTT GGT GTC CAA GGC TCA GGT TGG GGT TGG CTT GGT TTC AAT AAG GAA CGG GGA CAC TTA CAA ATT GCT GCT TGT CCA AAT CAG GAT CCA CTG CAA GGA ACA ACA GGC CTT ATT CCA CTG CTG GGG ATT GAT GTG TGG GAG CAC GCT TAC TAC CTT CAG TAT AAA AAT GTC AGG CCT GAT TAT CTA AAA GCT ATT TGG AAT GTA ATC AAC TGG GAG AAT GTA ACT GAA AGA TAC ATG GCT TGC AAA AAG TAA (SEQ ID NO:1)

A preferred polypeptide of the invention is represented as follows:

MLSRAVCGTS RQLAPALGYL GSRQKHSLPD LPY-
DYGALEP HINAQIMQLH HSKHHAAYVN NLNV-
TEEKYQ EALAKGELLE AIKRDFGSFD KFKEKL-
TAAS VGVQGSGWGW LGFNKERGHL
QIAACPNQDP LQGTTGLIPL LGIDVWEHAY
YLQYKNVRPD YLKAIWNVIN WENVTERYMA
CKK (SEQ ID NO:2)

In another embodiment, a nucleic acid probe comprising the exon 2-exon 4 junction of a nucleic acid molecule encoding the E3-protein is envisaged. The probe consists of at least 10 nucleotides, preferably between 11 and 2000 nucleotides. A particularly preferred probe includes the nucleotide sequence TAC CAG GAG GCG TTG GCC AAG GGG GAG TTG CTG GAA GCC ATC AAA (SEQ ID NO:3).

The present invention also includes polynucleotides where the coding sequence for the mature exon 3-deleted polypeptide may be fused in the same reading frame to a polynucleotide sequence which aids in the expression and/or secretion of a polypeptide from a host cell. The polynucleotides of the present invention may also have the coding sequence fused in frame to a marker sequence which allows for purification of the polypeptide of the present invention. The marker sequence may be a hexa-histidine tag supplied by pQE-9 vector to provide for purification of the polypeptide fused to the marker in the case of a bacterial host. Further, the marker sequence may be a hemagglutinin (HA) tag when a mammalian host is used (e.g., COS-7 cells). The HA tag corresponds to an epitope derived from the influenza hemagglutinin protein (Wilson et al., Cell 37:767, 1984, which is fully incorporated by reference).

The polypeptide and polynucleotides of the present invention are preferably provided in an isolated form, and are preferably purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide separated from some or all of the coexisting materials in the natural system is isolated. Such polynucleotides could be part of a vector and/or such polynucleotides or polypeptides could be part of a composition and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

"Host cells" used herein refer to cells comprising recombinant DNA molecules as a result of experimental transfection, transformation or infection, wherein "experimental" denotes an artificial means.

"Transformation" as used herein refers to introducing DNA into an organism so that the DNA is replicable, either as an extrachromasomal element or by chromosomal integration. "Transfection" as used herein refers to the introduction of DNA into a host cell whether or not any coding sequences are ultimately expressed. Methods of transfection and transformation are well know in the art. See, for example, Sambrook et al., In Molecular Cloning: A Laboratory Manual (2nd ed) (Ford et al. Eds) 1989, pages 1.74–1.84; 4.12, 4.37–4.38 and 16.30–16.55, Cold Spring Harbor Laboratory Press, Cold Spring Harbor, N.Y., all of which is fully incorporated by reference.

HEK293 tet-off cells are derived from human embryo renal cortical cells, wherein the cells have been transformed with a vector in which a recombinant molecule is under the negative control of the tetracyclin-based regulatory system. Such a system allows for the regulated expression of a recombinant protein by the administration of tetracycline or tetracyclin analogs (e.g., doxycyclin), whereby the presence of the antibiotic (or analog) represses the expression of the recombinant gene.

Host cells are genetically engineered (transduced, transfected or transformed) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the MnSOD E3(–) genes. The culture conditions, such as temperature, pH and the like, are those previously used with the host cell selected for expression, and will be apparent to the ordinary skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, non-chromosomal and synthetic DNA sequences, e.g., derivatives of SV40; bacterial plasmids; phage DNA; baculovirus; yeast plasmids; vectors derived from combinations of plasmid and phage DNA, viral DNA such as vaccinia, adenovirus, fowl pox virus and pseudorabies. However, any other vector may be used as long as it is replicable and viable in the host.

The appropriate DNA sequence may be inserted in the vector by a variety of procedures. In general, the DNA sequence is inserted into an appropriate restriction endonuclease site(s) by procedures known in the art. See, e.g., In Molecular Cloning: A Laboratory Manual (2nd ed) (Ford et al. Eds) 1989, pages 5.1–5.32, Cold Spring Harbor Laboratory Press, Cold Spring Harbor, N.Y.

Alternatively, DNA can be inserted by exploitation of non-template directed addition of nucleotides by thermostable polymerases during PCR. Such procedures and others are deemed to be within the scope of the skilled artisan.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a gel to isolate the desired fragment.

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Sambrook et al., *Molecular Cloning: A Laboratory Manual* (2nd ed) (Ford et al. Eds) 1989, pages 1.74–1.84; 4.12, 4.37–4.38 and 16.30–16.55, Cold Spring Harbor Laboratory Press, Cold Spring Harbor, N.Y., which is fully incorporated by reference). Unless otherwise provided, ligation may be accomplished using known buffers and conditions with 10 units to T4 DNA ligase ("ligase") per 0.5 $\mu$g of approximately equimolar amounts of the DNA fragments to be ligated.

The DNA sequence in the expression vector is operatively linked to an appropriate expression control sequence(s) to direct mRNA synthesis. "Operably linked" means that a polynucleotide sequence is placed into a functional relationship with another polynucleotide sequence (e.g., promoter linked to a polynucleotide encoding MnSOD E3(−)). Representative promoters are as follows: long terminal repeats (LTRs), SV40 promoter, *E. Coli* lac or trp or tac, phage lambda P[L] promoter and other promoters known to control expression of genes in prokaryotic and eukaryotic cells and their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for the eukaryotic cell culture, or such as tetracycline or ampicillin resistance in *E. Coli*.

The vector containing the appropriate DNA sequence as hereinabove described, as well as appropriate promoter control sequence, may be employed to transform an appropriate host to permit the host to express the protein. Representative host samples are as follows: bacterial cells, such as *E. Coli*, Steptomyces, *S. Typhimurium*, fungal cells such as yeast; insect cells such as Drosophila and Sf9; animal cells such as CHO, COS, HEK293; plant cells, etc. The selection of an appropriate host is well within the scope of the ordinary skilled artisan.

The present invention also includes recombinant constructs comprising one or more of the nucleic acid sequences as broadly described above. The constructs comprise a vector, such as a plasmid or viral vector, into which a nucleic acid sequence of the invention has been inserted, in a forward or reverse orientation. In a preferred aspect of this embodiment, the construct further comprises regulatory sequences, including for example, a promoter, operably linked to the sequence. Large numbers of suitable vectors and promoters are known to those skilled in the art, and they are commercially available. The following vectors are provided by way of example: Bacterial; pQE70, pQe60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pDR540, pRIT5 (Pharmacia). Eukaryotic; pWLNEO, pSV2CAT, pOG44, pXT1, pSG (Stratagene); pSVK3, pBPV, pMSG, pSVL (Pharmacia). However, any other plasmid or vector may be used as long as they are replicable and viable in the host.

Promoter regions can be selected from any desired gene using CAT (chloramphenicol acetyltransferase) vectors or other vectors with selectable markers. Two appropriate vectors are pKK232-8 and pCM7. Particular bacterial promoters include lacI, lacZ, T3, T7, SP6, gpt, Lambda P [L] and [R] trp and tac. Eukaryotic promoters include CMV, HSV thymidine kinase, early and late SV40, retroviral LTRs and metallothionein promoters. The selection of an appropriate promoter is well within the scope of the ordinary skilled artisan.

In a further embodiment, the present invention relates to host cells containing the above described constructs. The host cell can be a higher (e.g., mammalian cells) or lower eukaryotes (yeast cells) or prokaryotic (bacterial cells). Introduction of the construct into the host cell can be effected by calcium phosphate transfection, DEAE-Dextran mediated transfection or by electroporation (Davis et al., in Basic Methods in Molecular Biology, 1986).

The constructs in host cells can be used in a conventional manner to produce the gene product encoded by the recombinant sequence. Alternatively, the polypeptides of the invention can be synthetically produced by conventional peptide synthesizers.

Proteins can be expressed in mammalian cells, yeasts and bacteria, including other cells, under the control of appropriate promoters. Cell-free translation systems can also be employed to produce such proteins using RNAs derived from the DNA constructs of the present invention. Appropriate cloning and expression methodologies, including protein purification from inclusion bodies using prokaryotic hosts, are described in Molecular Cloning: A Laboratory Manual (2nd ed) (Ford et al. Eds) 1989, pages 17.37–17.41, Cold Spring Harbor Laboratory Press, Cold Spring Harbor, N.Y., herein fully incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, physical or chemical disruption of the cells, and further purification of the resulting crude extract.

Microbial cells employed in expression of proteins can be disrupted by any convenient method, including freeze-thaw cycling, sonication, mechanical disruption, or use of cell lysing agents; such methods are well know to those skilled in the art.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. It is preferred to have low concentrations (approximately 0.15–5 mM) of calcium ion present during purification (Price et al., J. Biol. Chem., 244:917 (1969)). Protein refolding steps can be used, as necessary, in completing configuration of the mature protein. Finally, high performance liquid chromatography (HPLC) can be employed for final purification steps.

Transgenic animals containing mutant, knock-out or modified genes corresponding to the cDNA sequences of SEQ ID NO: 1 or other sequences of the invention are also included. Transgenic animals are genetically modified animals into which recombinant, exogenous or cloned genetic material has been experimentally transferred. Such genetic material is often referred to as a "transgene". The nucleic acid sequence of the transgene, in this case a form of SEQ ID NO: 1, may be integrated either at a locus of a genome where that particular nucleic acid sequence is not otherwise normally found or at the normal locus for the transgene. The transgene may consist of nucleic acid sequences derived from the genome of the same species or of a different species than the species of the target animal.

The term "germ cell line transgenic animal" refers to a transgenic animal in which the genetic alteration or genetic information was introduced into a germ line cell, thereby conferring the ability of the transgenic animal to transfer the genetic information to offspring. If such offspring in fact possess some or all of that alteration or genetic information, then they too are transgenic animals. In a related aspect, in order to control transgenic expression in mammalian cells, several systems are now available that enable transcription of a gene to be controlled using small molecules (e.g., tetracycline; see Clackson T., Curr Opin Chem Biol (1997) 1(2): 210–218).

The alteration or genetic information may be foreign to the species of animal to which the recipient belongs, foreign only to the particular individual recipient, or may be genetic information already possessed by the recipient. In the last case, the altered or introduced gene may be expressed differently than the native gene. Transgenic animals can be produced by a variety of different methods including transfection, electroporation, microinjection, gene targeting in embryonic stem cells and recombinant viral and retroviral infection (see, e.g., U.S. Pat. No. 4,736,866; U.S. Pat. No. 5,602,307; Mullins et al. (1993) Hypertension 22(4):630–633; Brenin et al. (1997) Surg. Oncol. 6(2)99–110; Tuan (ed.), Recombinant Gene Expression Protocols, Methods in Molecular Biology No. 62, Humana Press (1997)).

A number of recombinant or transgenic mice have been produced, including those which express an activated oncogene sequence (U.S. Pat. No. 4,736,866); express simian SV 40 T-antigen (U.S. Pat. No. 5,728,915); lack the expression of interferon regulatory factor 1 (IRF-1) (U.S. Pat. No. 5,731,490); exhibit dopaminergic dysfunction (U.S. Pat. No. 5,723,719); express at least one human gene which participates in blood pressure control (U.S. Pat. No. 5,731,489); display greater similarity to the conditions existing in naturally occurring Alzheimer's disease (U.S. Pat. No. 5,720,936); have a reduced capacity to mediate cellular adhesion (U.S. Pat. No. 5,602,307); possess a bovine growth hormone gene (Clutter et al. (1996) Genetics 143(4):1753–1760); or, are capable of generating a fully human antibody response (McCarthy (1997) The Lancet 349(9049):405).

While mice and rats remain the animals of choice for most transgenic experimentation, in some instances it is preferable or even necessary to use alternative animal species. Transgenic procedures have been successfully utilized in a variety of non-murine animals, including sheep, goats, pigs, dogs, cats, monkeys, chimpanzees, hamsters, rabbits, cows and guinea pigs (see, e.g., Kim et al. (1997) Mol. Reprod. Dev. 46(4):515–526; Houdebine (1995) Reprod. Nutr. Dev. 35(6):609–617; Petters (1994) Reprod. Fertil. Dev. 6(5):643–645; Schnieke et al. (1997) Science 278(5346):2130–2133; and Amoah (1997) J. Animal Science 75(2):578–585).

The method of introduction of nucleic acid fragments into recombination competent mammalian cells can be by any method which favors co-transformation of multiple nucleic acid molecules. Detailed procedures for producing transgenic animals are readily available to one skilled in the art, including the disclosures in U.S. Pat. No. 5,489,743 and U.S. Pat. No. 5,602,307.

Amplification of nucleic acids by polymerase chain reaction is also included in the invention. The technique of "polymerase chain reaction," or "PCR," as used herein generally refers to a procedure wherein minute amounts of a specific piece of nucleic acid, RNA and/or DNA, are amplified as described in U.S. Pat. No. 4,683,195. Generally, sequence information from the ends of the region of interest or beyond needs to be available, such that oligonucleotide primers can be designed; these primers will be identical or similar in sequence to opposite strands on the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See, generally, Mullis et al., Cold Spring Harbor Symp. Quant. Biol., 51:263 (1987); Erlich, ed., PCR Technology, (Stockton Press, N.Y., 1989). As used herein, PCR is considered to be one, but not the only, example of a nucleic acid polymerase reaction method for amplifying a nucleic acid test sample, comprising the use of a known nucleic acid (DNA or RNA) as a primer.

"Nested PCR" as used herein refers to the use of two sets of primers to amplify a specific target template, wherein the first set of primers flank the target template and the second set of primers are internal to the first and further comprise 3' proximal sequences of the first primer contiguous with template specific sequences of the target.

A "primer" or "oligonucleotide" can be a single-stranded polynucleotide that may be chemically synthesized by known methods. Suitable oligonucleotides may be prepared by the phosphoramidite method described by Beaucage and Carruthers, Tetr. Lett., 22:1859 (1981), or by the triester method, according to Matteucci et al., J. Am. Chem. Soc., 103:3185 (1981), or by other methods such as by using commercial automated oligonucleotide synthesizers such as Applied Bio Systems oligonucleotide synthesizer, according to the specifications provided by the manufacturer.

This invention provides methods of screening drugs to identify those which modulate (e.g., enhance (agonists) or block (antagonists/inhibitors)) the activity of MnSOD E3 (−). As an example, a mammalian cell expressing MnSOD E3 (−) would be incubated in the presence of a drug. The ability of the drug to enhance or block MnSOD E3 (−) activity (e.g., effect non-specific mtDNA oxidative damage) could then be measured.

In one embodiment, a nucleic acid probe as described herein is useful for identifying an agent that modulates the expression of a nucleic acid molecule encoding an MnSOD E3(−) polypeptide. The modulation of expression is identified by first exposing the agent to cells that express the nucleic acid molecule. Tetracycline, for example, can be used to modulate expression. After exposing the cells to the agent, modulation of expression is determined by measuring the quantity of MnSOD E3(−) expressed. Techniques to detect RNA species include, for example, Northern hybridization, RNase (nuclease) protection and RTIPCR.

A nucleic acid probe is also useful in diagnosing oxidative stress and cellular conditions associated with oxidative stress, such as necrosis, apoptosis, damaged mitochondrial constituents, viral replication and infectious agent replication. Diagnosis of oxidative stress, for example, can be achieved by exposing a cell or tissue sample to an agent that specifically binds to a nucleic acid molecule encoding the MnSOD E3(−) polypeptide. Preferably, the agent is a nucleotide primer, but could also be a nucleic acid (single stranded RNA or DNA) which spans the MnSOD E2–E4 mRNA splice junction. Following the exposure step, a determination that the agent has specifically bound to the nucleic acid molecule indicates a positive diagnosis of oxidative stress in the sample. To make a determination of whether binding has occurred, standard techniques, such as RT/PCR, RNase or other nuclease protection can be employed. RT/PCR has been described.

Diagnosing oxidative stress can alternatively be diagnosed by exposing a cell or tissue sample to an agent that specifically binds an MnSOD E3(−) polypeptide. Preferably, the agent is an antibody, but could also be a flourescence or other light-based detection system. More preferably, the agent is an antibody that specifically binds to the exon 2-exon 4 junction of the MnSOD E3(−) polypeptide. Particularly preferred is an antibody that binds to the LeuAla-LysGlyGluLeu (SEQ ID NO:9) sequence of the junction. Techniques for raising antibodies to polypeptides are well known in the art.

In another embodiment, cell death is promoted by modulating the level of a nucleic acid encoding the MnSOD E3(−) polypeptide. Modulating the level of the nucleic acid is preferably achieved by exposing a cell to an expression construct carrying the nucleic acid. The delivery of expression constructs to specific cells, such as the cells of a tumor, is well known in the art. See U.S. Pat. No. 5,698,443, for example, which is incorporated herein by reference.

Alternatively, cell death is promoted by exposing a cell to a polypeptide encoded by a nucleic acid molecule encoding the MnSOD E3(−) polypeptide.

On the other hand, cell death is inhibited by impeding the expression of a nucleic acid molecule encoding the MnSOD E3(−) polypeptide. Impeding expression is preferably achieved using an antisense nucleic acid molecule.

The present invention is also directed to antagonist/inhibitors of the polypeptides of the present invention. The antagonist/inhibitors are those which inhibit or eliminate the function of the polypeptide in vivo or in vitro.

Antagonists may bind to a polypeptide of the present invention and eliminate its function. The antagonist, for example, could be an antibody against the polypeptide or, in some cases, an oligonucleotide.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96). All of these techniques are incorporated herein by reference.

Techniques described in U.S. Pat. No. 4,946,778, incorporated herein by reference, for the production of single chain antibodies can be adapted to produce single chain antibodies to immunogenic polypeptide products of this invention.

Another example of an inhibitor is an antisense construct. Antisense technology can be used to control gene expression through triple-helix formation or antisense DNA or RNA. Both methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251:1360 (1991)), all of which are incorporated herein by reference, thereby preventing transcription and the production of MnSOD E3 (−). The antisense RNA oligonucleotide hybridizes to the mRNA in vivo and blocks translation of the mRNA molecule into the MnSOD E3 (−) polypeptide. These techniques are described by Okano, *J Neurochem*, 56:560 (1991) and Oligodeoxynucleotides as Antisense Inhibitors of Gene Expression, CRC Press, Boca Raton, Fla. (1988), both of which are incorporated herein by reference.

For a review of antisense therapy, see, e.g., Uhlnann et al., Chem. Reviews, 90:543–584 (1990). RNA oligonucleotides can be provided in the form of ribozymes designed to cleave the mRNAs to which they bind. The ribozymes will comprise RNA or mixed RNA-DNA oligonucleotide.

A preferred embodiment of the invention is the treatment of diseases in which apoptosis is dysregulated. The treatments will have the potential to change the natural progression of some of these diseases. Such therapeutic treatments will involve either the induction or the inhibition of apoptosis through MnSOD E3 (−), depending on the particular disease condition.

The MnSOD E3 (−) polypeptides of the present invention may be employed in accordance with the present invention by expression of such polypeptides in vivo, which is often referred to as "gene therapy." For example, cells from a patient may be engineered with a polynucleotide encoding a polypeptide ex vivo, with the engineered cells then being provided to a patient to be treated with the polypeptide. Such methods are well known in the art. For example, cells may be engineered by procedures known in the art (see, e.g., U.S. Pat. No. 5,672,510, incorporated herein by reference) by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus. An adenovirus, for instance, may be used to engineer cells in vivo after combination with a suitable delivery vehicle.

Drug delivery vehicles such as liposomes can be used to deliver and provide sustained release of the formulations in the body. The liposomes can have targeting moieties exposed on the surface such as antibodies, ligands or receptors to specific cell surface molecules. For example, it may be desirable to limit the delivery of the formulation to only tumor cells. Such cells can be targeted to receive the therapeutic formulation by incorporating into the liposome carrier, a targeting moiety that recognizes and binds a specific tumor surface marker. Liposome drug delivery is known in the art (see, e.g., Biochimica et Biophysica Acta, 113:201–227 (1992), incorporated herein by reference).

The quantities of reagents determined to be an effective amount for treatment will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman et al. (eds), Goodman and Gilman's: The Pharmacological Bases of Therapeutics, 8th Ed. (1990), Pergamon Press; and Remington's Pharmaceutical Sciences, 17th Ed. (1990), Mack Publishing Co., Easton, Pa. Methods for administration are discussed therein, e.g., for oral, intravenous, intraperitoneal, or intramuscular administration, transdermal diffusion, and others.

The polypeptides of the present invention may be employed in combination with a suitable pharmaceutical carrier. Such compositions comprise a therapeutically effective amount of the polypeptide, and a pharmaceutically acceptable carrier or excipient. Such a carrier includes, but is not limited to, saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The amounts and dosage regimens of MnSOD E3 (−) and administered to a subject will depend on a number of factors such as the mode of administration, the nature of the condition being treated and the judgment of the prescribing physician. Generally speaking, they are given, for example, in therapeutically effective doses of at least about 0.1–10 $\mu$g/kg body weight and in most cases they will be administered in an amount not in excess of about 8 mg/kg body weight per day and preferably the dosage is from about 1 mg/kg to about 10 mg/kg body weight daily, taking into account the routes of administration, symptoms, etc.

If the pharmaceutical composition is formulated for oral delivery and contains a peptide or peptide-like compound as the active agent, then the formulation must include a means for protecting the agent from the proteolytic enzymes of the digestive system. Typically, the agent is encased in a liposome structure or chemically derivatized so that the enzymes are prevented from cleaving the amide bonds of the peptide, resulting in the agent's degradation.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, preferably about 20% (see, Remington's, supra).

The compositions containing the compounds can be administered for prophylactic and/or therapeutic treatments. In therapeutic applications, compositions are administered to a patient already suffering from a disease, as described above, in an amount sufficient to cure or at least alleviate the symptoms of the disease and its complications. An amount adequate to accomplish this is defined as "therapeutically effective dose." Amounts effective for this use will depend on the severity of the disease and the weight and general state of the patient.

In prophylactic applications, compositions containing the compounds of the invention are administered to a patient susceptible to or otherwise at risk of a particular disease. Such an amount is defined to be a "prophylactically effective dose." In this use, the precise amounts again depend on the patient's state of health and weight.

The present invention will be further described with reference to the following illustrative examples; however, it is to be understood that the present invention is not limited to such examples. All parts or amounts, unless otherwise specified; are by weight. All references, patents or other documents referred to in this application are herein incorporated by reference in their entirety.

EXAMPLE 1

Identification of a Novel MnSOD E3 (−) mRNA Splice Variant Associated With Multiple mtDNA Deletions MnSOD mRNA transcripts from the PMBC of a patient with mild anemia, mild leukopenia and multiple mtDNA deletions in his PMBC were initially analyzed by cloning reverse transcriptase/polymerase chain reaction (RT/PCR) products. Cells were isolated from 10 ml of freshly isolated blood ("purple-top" EDTA vacutainer tube) using Lymphocyte Separation Medium (Pharmacia). Washed cells were lysed by the TriZol method (GIBCO/BRL). Total RNA was then re-extracted with acidic phenol and alcohol precipitated. cDNA was prepared using M-MLV reverse transcriptase (BRL) and oligo dT.

Nested PCR was used in order to obtain a more effective amplification. Two PCR rounds were performed: MnSOD primer pair #1: Exon-1-forward: 5'-AGCCAGCTCTAGAAGCATGTTGAG (SEQ ID NO:5), Exon-5-reverse: 5'-ATTCTGCAGTACTCTAGACCACTAC (SEQ ID NO:6); nested 2nd primer pair: Exon-2-for: 5'-GCTCTAGAACCTCACATCAAC (SEQ ID NO:7); Exon-4-rev: 5'-TTTCTAGAGCCTTGGACACCAACAG (SEQ ID NO:8). Labeled P-32 primers were used in the second, nested PCR. PCR products were denatured and run on a 49:1 acrylamide:bis urea denaturing gel for 1.5 hr at 400 V, running buffer tris-borate-EDTA (TBE).

FIG. 2 shows RT/PCR products for controls 1–8 and 11–13 and for samples 10–11. The controls in lane 1–2 are the full-length MnSOD cDNA and the MnSOD E3 (−) CDNA recombinant plasmids, respectively. The PMBC controls, lanes 3–8, exhibit the normal E2/E3/E4 MnSOD mRNA splicing pattern. PMBC RNA from the Chilean proband with multiple mtDNA deletions, lane 9, revealed equal amounts of the E2/E4, 215 bp RT/PCR product to the E2/E3/E4, 331 bp fragment. RT/PCR analysis using total PMBC RNA from an acute mononucleosis patient, lane 10, showed comparable levels of the 331 bp (E2/E3/E4) and the 215 bp (E2/E4) MnSOD RT/PCR products. Notably, lane 11, PMBC from the same patient 6 months prior to latent infectious mononucleosis diagnosis, shows the absence of the E2/E4 product.

DNA sequencing was conducted for the RT/PCR MnSOD splice variants expressed in the patient with acute infectious mononucleosis described in FIG. 2 (lane 10), above. The radioactive RT/PCR 215 bp product was excised from the gel and reamplified by PCR. The reamplified DNA was used as the template for PCR-cycle sequencing (Perkin-Elmer) along with the MnSOD gene-specific primers described above.

Figure 1B:
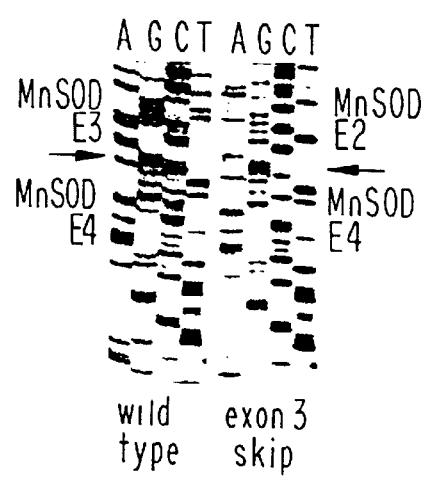
FIG. 1B shows a DNA sequencing gel of two cDNA recombinants obtained from the RT/PCR of patient MnSOD.
Figure 1C:
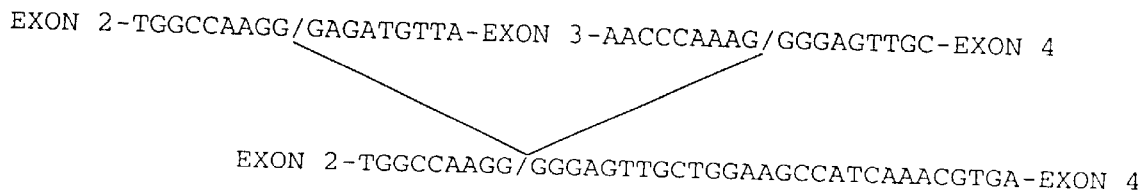
FIG. 1C shows a schematic representation comparing an abbreviated full-length MnSOD cDNA (SEQ ID NOS: 12 and 13) to an abbreviated MnSOD E3(−) cDNA (SEQ ID NO: 14).
Figures 3A, 3B:
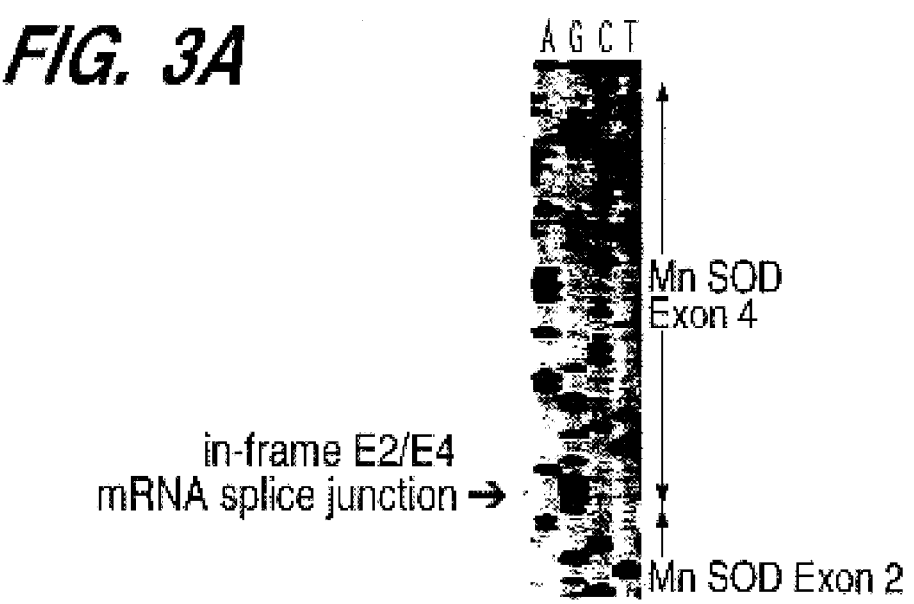
FIG. 3A shows a sequencing gel of MnSOD E3(−) (215 bp) from the RT/PCR product of PMBC from a patient with acute infectious mononucleosis.
FIG. 3B shows a schematic polynucleotide showing the exon 2-exon 4 junction of FIG. 3A. The DNA sequence shown corresponds to nucleotides 10–39 of SEQ ID NO: 3, and the protein sequence shown corresponds to amino acids 3–12 of SEQ ID NO: 4.

FIG. 1A shows Southern hybridization analysis using a full-length mtDNA P-32 probe. FIG. 1B shows DNA sequencing of two RT/PCR recombinant clones: the normal MnSOD mRNA and the MnSOD E3(−). FIG. 1C is a schematic comparison of the fill length MnSOD amino acid sequence to that of the splice variant.

EXAMPLE 2

In vitro Expression of the cDNA of the MnSOD E3 (−) Splice Variant and its Effect on mtDNA and Nuclear DNA Degradation The effect on the genomic structure of cellular DNA by expression of the cDNA encoding the E3(−) MnSOD isoform was examined using the tet-off mammalian gene expression system (Clontech).

Transient transfection of HEK293 tet-off cells with the full length, antioxidant-MnSOD or the MnSOD E3(−) cDNA are shown in FIGS. 5A and 5B. Both cDNAs are driven by the tetracycline/doxycycline-regulated transcription factor (Clontech). HEK293 tet-off cells were grown in DMEM/5%FBS with 20 ng/ml doxycycline and then electroporated with 1 mg recombinant plasmid per $10^8$ cells. Electroporated cells were split into four 60 mm plates and grown for 30 hrs in the same medium. The medium in each plate was replaced with DMEM/5%FBS with either 20 ng/ml, 2.0 ng/ml, 0.2 ng/ml, 0.02 ng/ml doxycycline. Cell growth was continued for 24 hours to allow expression of the transfected cDNA. Total cellular DNA was isolated using the non-phenolic, PureGene method.

1 mg of DNA was digested with either BamHI (FIG. 5A) or PvuII (FIG. 5B). The digested DNA was electrophoresed onto a 0.7% agarose gel, and treated for Southern hybridization. Nylon filters containing the electrophoresed DNA was probed with a mtDNA fragment from hmt6900 to hmt9100. Shown at the bottom of FIG. 5B is PvuII-digested DNA probed with a nuclear rDNA fragment.

These gels suggest the generation of hydroxyl free radicals (Fenton-like reaction) causing degradation of mtDNA that is "smeared" due to the random, non-specific attack of the hydroxyl radical on DNA. Because culture conditions used in the transfection lacked selenium, an important component to rid cells of hydrogen peroxide, generation of hydroxyl free radicals is likely. Expression of the MnSOD E3(−) isoform generates a degradation pattern similar to the normal MnSOD cDNA transfections, but with at least two differences: first, the DNA degradation with MnSOD E3(−) expressed includes nuclear degradation; second, the cDNA appears to be discrete mtDNA fragments (denoted by *), which are similar to the multiple mtDNA deletions in the studies patient (FIG. 1).

Figure 6:
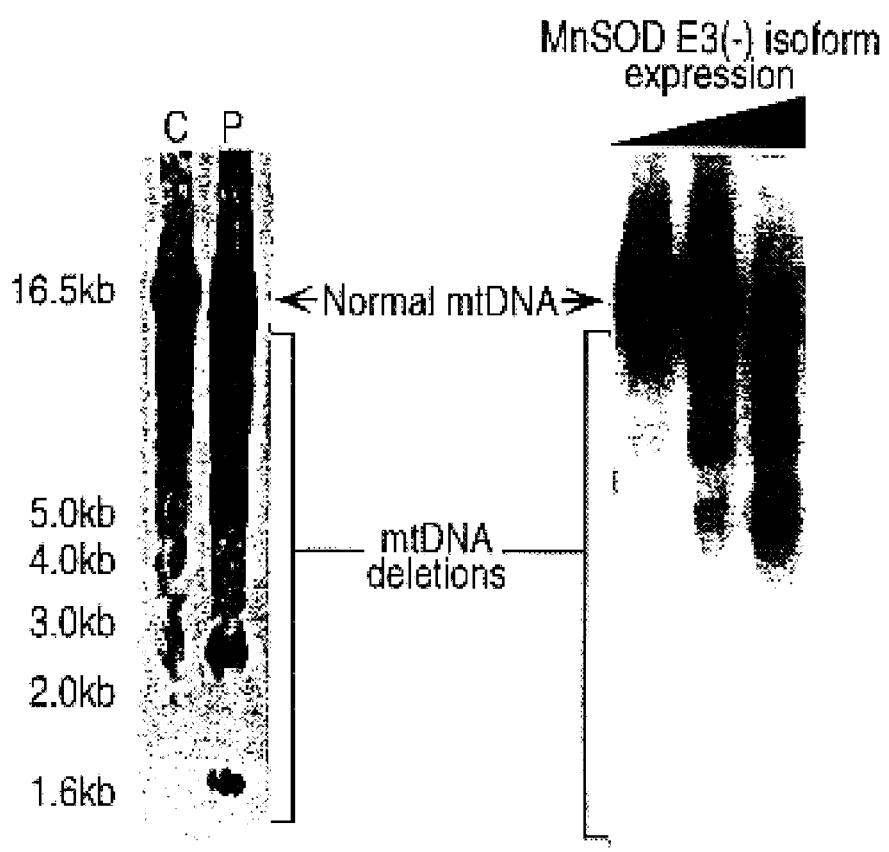
FIG. 6 compares Southern hybridization gels of PMBC MnSOD E3(−) of a proband with mild Pearson's Syndrome and MnSOD E3(−) of HEK 293 tet-off cells supplemented with selenium.

FIGS. 6A and 6B are the results of transfection with MnSOD E3 (−) Increased expression of the MnSOD E3(−) cDNA results in a similar mtDNA fragmentation and/or deletion pattern as seen in the original Southern analysis of mtDNA of a Chilean proband with mild leukopenia (FIG. 6A).

The mtDNA deletions caused by the expression of MnSOD are shown in FIG. 6B. The expression of the MnSOD E3 (−) cDNA was induced in HEK 293 tet-off cells supplemented with selenium. For the HEK 293 tet-off, MnSOD E3(−) cDNA transfection, cells were trypsinized 12 hr after electroporation and replated in order to completely remove dead cells. HEK293 tet-off transfected cells were always kept at fully-repressing culture conditions (20 ng/ml doxycycline). At 30 hr post-transfection, cDNA expression was induced for 6 hr by varying the amount of doxycycline in the culture: 20 ng/ml doxycycline (lane 1, fully repressed), 2.0 ng/ml doxycycline (lane 2), and 0.2 ng/ml doxycycline (lane 3).

Human mtDNA P-32 labeled hybridization probes were from hmt 15,360–hmt 740 (the D-loop region) and from hmt 6900–hmt 9020 (COI, COII, and ATPase 6). Lanes C and P of FIG. 6A are healthy control and patient PMBC DNA samples. Transfection control analysis included Southern probing for plasmid sequences and assaying for the expression of reporter gene B-galactosidase.

EXAMPLE 3

Preparation and Use of Polyclonal Antiserum Containing Anti-MnSOD E3(−) Antibodies Antibody Preparation A polyclonal antibody was raised in rabbits using the peptide sequence: $NH_2$-(GlyCys)-GlnGluAlaLeuAlaLysGlyGluLeuLeuGluAla (vendor: BioSynthesis, Inc. Project #: BSYN 617,618. The N-terminal GlyCys are not MnSOD-encoded sequence, and are part of this peptide sequence for technical reasons).

Antibodies were prepared according to the following protocol:

The animals used were two New Zealand White Females, approximately 12 weeks of age, 2 kg of weight. Two (2) antigen-adjuvants compositions were used. For primary injection, (1:1) 200 μg of conjugated peptide (~0.5 ml of conjugate solution) plus equal amount of Freund's complete adjuvant was used. For booster injection, (1:1) 200 μg of conjugated peptide (~0.5 ml of conjugate solution) plus equal amount of Freund's incomplete adjuvant was used. Animals were inoculated according the following schedule:

| DAY | PROCEDURE | AMOUNTS/VOLUMES PER RABBIT (Serum Volumes are approximate) |
|---|---|---|
| 0 (week 0) | Pre-bleed Primary Injection | 2.0–5.0 ml of SERUM (1:1) conjugate solution:Freund's Complete |
| 14 (week 2) | First Booster | (1:1) conjugate solution:Freund's Incomplete |
| 28 (week 4) | Second Booster | (1:1) conjugate solution:Freund's Incomplete |
| 42 (week 6) | Third Booster First Production Bleed Perform ELISA on this serum | (1:1) conjugate solution:Freund's Incomplete 20 ml of SERUM |
| 56 (week 8) | Fourth Booster Second Production Bleed | (1:1) conjugate solution:Freund's Incomplete 20 ml of SERUM |
| 70 (week 10) | Third Production Bleed | 20 ml of SERUM |

The MnSOD E3(−) antibody was affinity purified from serum by binding the antibody to a peptide column containing the aforementioned peptide (Sulfo-Link, Pierce), and eluting the antibody with 0.1 M Glycine pH 3.0.

Western Blotting of Human MnSOD Protein

The gels were electro-blotted according to Towbin et al., Proc Natl Acad Sci USA (1979) 76(9):4350–54, incorporated herein by reference. Nitrocellulose blots were first incubated with goat anti-human MnSOD antibody (R&D Systems) or rabbit anti-MnSOD E3(−) antibody (1:10,000 dilution) and then with a donkey anti-goat IgG-horseradish peroxidase (HRP) conjugate (dilution 1:10,000) or with a goat-anti-rabbit IgG-HRP conjugate (dilution 1:10000) as secondary antibodies, respectively. Enhanced chemiluminescence was used as a detection system (Pierce). Each lane received the protein content of 2×105 cells.

In order to produce proteins containing the normal MnSOD and MnSOD E3(−) sequences, E. coli strain BL21 was transformed with the appropriate MnSOD recombinant DNA (vector: pRSET-B (Invitrogen)) and the expression of each MnSOD-protein was induced using IPTG. After induction, 10 mls of cells were pelleted and lysed in 100 ml of 2×Laemmli SDS-buffer at 100° C. for 5 minutes. 10 ml of each protein sample was separated by SDS-PAGE, transferred electrophoretically to nitrocellulose, and probed by western analysis (described in greater detail below) by using either the MnSOD E3(−) antibody or an antibody against normal MnSOD (R&D Systems).

Figure 8:
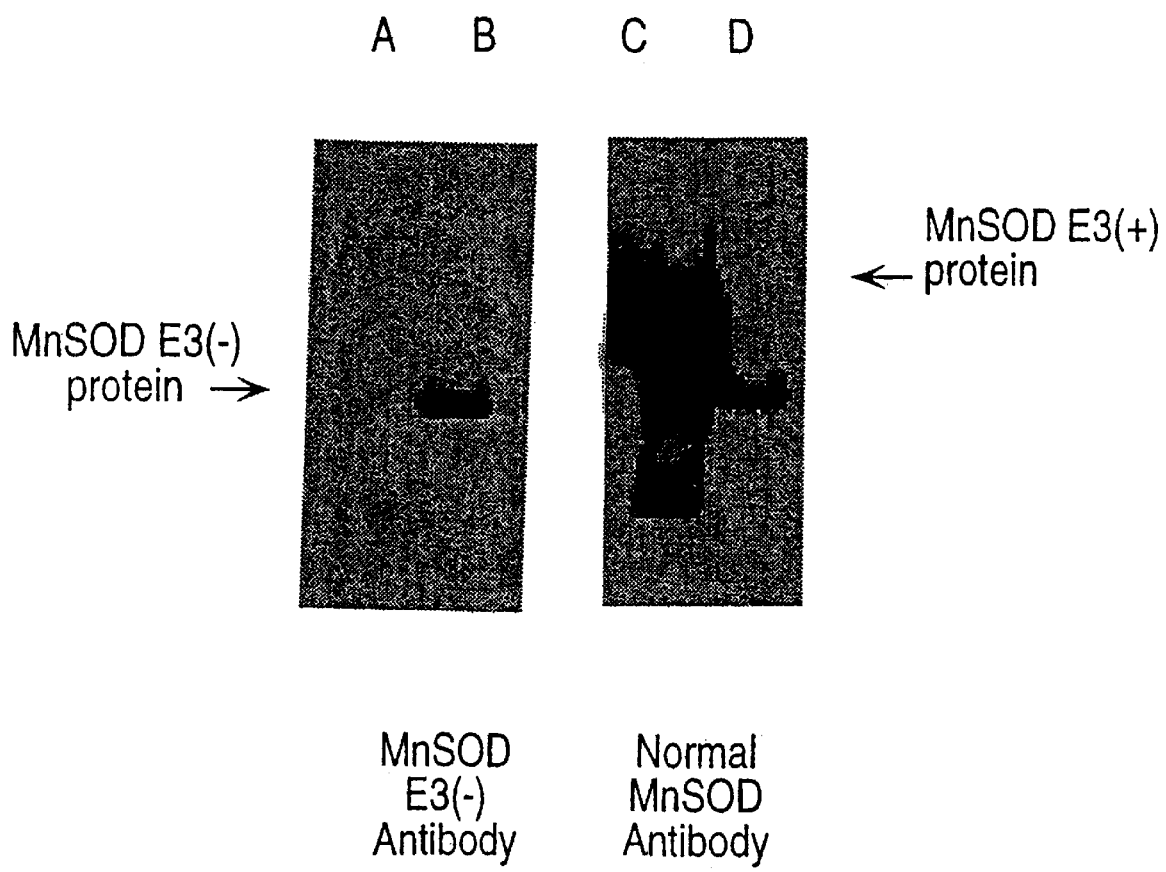
FIG. 8 shows a western analysis of an *E. coli* extract containing MnSOD E3(−) polypeptide (lanes A and C) and an *E. coli* extract containing normal MnSOD (lanes B and D). The extracts were probed using either an MnSOD E3(−) antibody (lanes A and B) or an antibody against normal MnSOD (lanes C and D).
Figure 9:
FIG. 9 shows a Western analysis of PMBC protein extracts from control (lane 1) and HIV(+) (lane 2) patients. The extracts were probed using either an MnSOD E3(−) antibody (bottom) or an antibody against normal MnSOD (top).
Figure 9:

Western blots are shown in FIG. 8 comparing E. coli extracts containing either MnSOD E3(−) or normal MnSOD. Additional blots are shown in FIG. 9 for PMBC protein extracts of an HIV(+) patient and a control.

Total cellular protein was prepared from peripheral mononuclear blood cells (PMBCs) as follows. 10 mls of blood were drawn in a purple-top, EDTA vacutainer tube, diluted twofold with HANK's 1×buffer, and banded on a Percoll-Plus gradient according to manufacturer's directions (Pharmacia). Cells were continually maintained in serum during isolation. Cells were pelleted and quickly lysed by boiling at 100° C. for 5 min in sample buffer containing 2% mercaptoethanol.

Electrophoresis and Western blotting of MnSOD proteins were performed as follows. SDS-polyacrylamide gel electrophoresis (SDS-PAGE) was carried out using a minigel apparatus (Bio-Rad, Hercules, Calif.) according to Laemmli, "Cleavage of Structural proteins during the assembly of the head of bacteriophage T4", Nature (1970) 227: 680–85, incorporated herein by reference. Proteins were separated in a 12% Tris-glycine SDS-PAGE gel. This gel system does not resolve the normal MnSOD protein from the MnSOD E3(−) isoform. It should be noted that precursor and mature MnSOD proteins are known to run aberrantly. See, e.g., Wispe et al., Synthesis and processing of the precursor for human mangano-superoxide dismutase, *Biochim Biophys Acta* (1989) 994(1):30–36.

Detection of MnSOD E3(−) Using an ELISA Assay

In order to measure the presence or absence of MnSOD E3(−) in a sample, an ELISA assay is performed as described, for example, in U.S. Pat. No. 4,016,043, herein fully incorporated by reference. Briefly, an antibody directed to the exon 2/4 epitope of MnSOD E3(−) is bound to the surface of a solid phase. A sample suspected of comprising MnSOD E3(−) is contacted with the bound antibody under appropriate conditions for antibody-antigen binding. The antibody-containing surface of the solid phase is washed by an appropriate buffer having a non-specific blocking agent. Thereafter, a secondary antibody having a covalently linked enzyme is contacted with the antibody-containing surface under conditions appropriate for antibody-antigen binding. After washing, the antibody-containing surface of the solid phase is contacted with a reagent that serves as a substrate for the linked enzyme such that upon reaction between enzyme and substrate the enzyme activity is proportional to the presence and quantity of MnSOD E3(−) in the sample.

EXAMPLE 4

Isolation and Use of Nucleic Acids

RNA and DNA Preparation and mtDNA Detection

Total cellular RNA was prepared from peripheral mononuclear blood cells (PMBCs) as follows. 10 mls of blood were drawn in a purple-top, EDTA vacutainer tube, diluted twofold with HANK's 1×buffer, and banded on a Percoll-Plus gradient according to manufacturer's direction (Pharnacia). Cells were continually maintained in serum during isolation. Cells were pelleted and quickly lysed with 2 ml of Trizol (GIBCO/BRL). After 5 min at room temperature, the lysed solution was mixed with 0.2 vol of chloroform, mixed and microfuged for 10 min. The aqueous phase was removed and 0.6 vol of isopropanol was added, mixed and total ribonucleic acids were precipitated at room temperature for 15 min. RNA was pelleted by microcentrifugation for 10 min, and the pellet was resuspended in 0.5 ml of water. This solution was then extracted with acidic phenol (Ambion). RNA was precipitated by adding one-tenth volume of 3M sodium acetate and 2–3 volumes of ethanol. After 10 min at −70° C., the RNAs were pelleted and dissolved in 100 µl of water.

Total cellular DNA was isolated using the PureGene Isolation system (Gentra), which is a non-phenolic isolation method. For mitochondrial (mt) DNA analysis, the DNA was digested with the restriction endonuclease, PvuII, and the products were separated using 0.7% agarose. The agarose gel was treated for Southern Hybridization analysis. MtDNA sequences were detected using a P-32 probe containing the human mtDNA D-loop spanning nucleotides 15,340 to 710.

RT/PCR Analysis of the Human MnSOD mRNA

Total cellular RNA was reverse transcribed with 10 Units of Superscript (Gibco/BRL) and 1 microgram of oligo-dT according to manufacturer's directions. After reverse transcription, the human MnSOD cDNA was amplified by the polymerase chain reaction (PCR) amplification cycles were: denaturation: 1 min at 95° C., annealing for 0.5 min at 55° C., and DNA synthesis for 1 min at 72° C. After PCR amplification, the amplified products were separated by using a 0.7% low-melt agarose gel and the desired 700 bp cDNA product was eluted using agarose (NEBioLabs). The isolated PCR product was digested with the restriction enzyme XbaI and subcloned into the vector pGEM-9Zf (Promega). For nested PCR, 1 µl of the first reaction was added to a fresh amplification mix containing a second set of oligonucleotide primers that were end-labeled with P-32.

The oligonucleotide primer pairs used in the RT/PCR analyses were the following:

1. Cloning the normal and E3(−) MnSOD cDNA:
   MnSOD-1-f: 5'-AGCCAGCTCTAGAAGCATGTTGAG (SEQ ID NO:10) &
   MnSOD-710-r: 5'-ATTCTGCAGTACTCTAGACCACTAC (SEQ ID NO:11)

2. Examination of the mRNA splicing pattern between MnSOD E2 and E4 by nested PCR:
   a. MnSOD-1-f: 5'-AGCCAGCTCTAGAAGCATGTTGAG (SEQ ID NO:10) &
   MnSOD-710-r: 5'-ATTCTGCAGTACTCTAGACCACTAC (SEQ ID NO:11)
   b. MnSOD-130-f: 5'-GCTCTAGAACCTCACATCAAC (SEQ ID NO:7) &
   MnSOD-410-r: 5'-TTTCTAGAGCCTTGGACACCAACAG (SEQ ID NO:8)

The P32-products from the nested PCR reactions were examined by 5% denaturing PAGE gels and exposed to X-Omat x-ray film. Ratios of MnSOD E2/E3/E4 & E2/E4 Rt/PCR products were quantified by Molecular Imager (BioRad). Negative controls were always done alongside of these PCRS.

Figure 4:
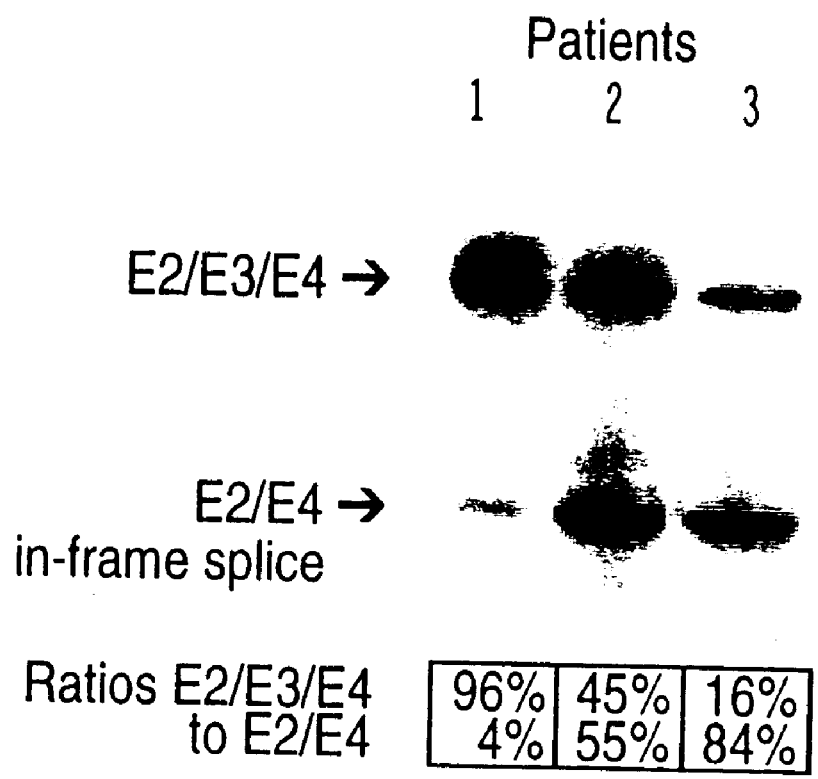
FIG. 4 compares RT/PCR products of MnSOD and MnSOD E3(−) from a PMBC sample from three asymptomatic HIV-infected patients.

FIG. 4 shows moderate to high levels of expression of the MnSOD E3(−) mRNA splice variant in PMBCs of asymptomatic HIV-infected patients 2 and 3. Patient 3, who exhibited high levels of the MnSOD E3(−) splice variant, had received the 1997/1998 flu vaccine (Trivalent '97/'98) three days prior to the RT/PCR analysis.

Figure 7:
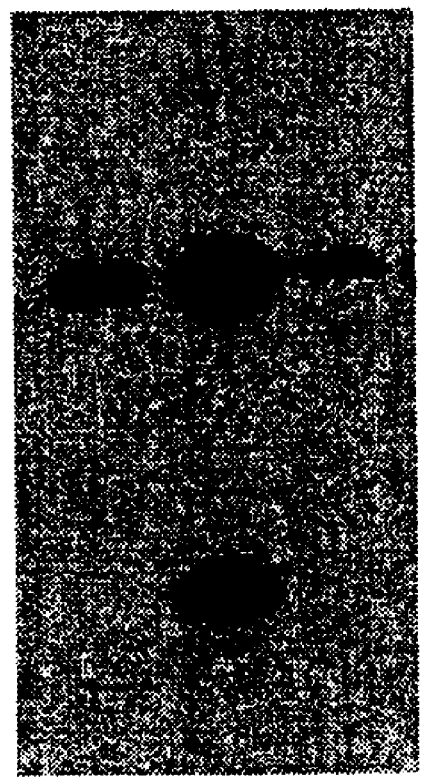
FIG. 7 shows the RT/PCR products of MnSOD and MnSOD E3(−) from a PMBC sample from a healthy patient, before (lane 1), 6 hours after (lane 2), and 6 days after (lane 3) receiving a flu vaccination.

In FIG. 7, expression of the MnSOD E3(−) splice variant was induced prior to and after receiving a Trivalent '97/'98 flu vaccine in PMBCs of a healthy individual. RT and nested PCR analysis was done as described in FIG. 2. Lane 1 is prior to flu vaccination, lane 2 is 6 hours post, and lane 3 is 6 days post.

DNA Sequence Analysis

The MnSOD cDNA recombinant plasmids were sequenced by the dideoxy method using the AmpliCycle Sequencing kit (Perkin Elmer).

EXAMPLE 5

Oxidized Protein Analysis

Western Analysis of Oxidized Proteins

Western analysis of oxidized proteins in immune activated PMBCs and Jurkat T cells transfected with the MnSOD E3(−) recombinant DNA, pBI-G/MnSOD E3(−) was conducted.

The tet(tetracycline) or dox (doxycline) regulated plasmid, pBI-G (Clontech) was used in the construction of pBI-G/MnSOD E3(−). This is a bidirectional promoter plasmid and uses a CMV promoter which is under the control of tetracycline (see tet-regulated plasmids, Clontech). pBI-G/MnSOD E3(−) was used in all cell culture transfections.

Figure 10:
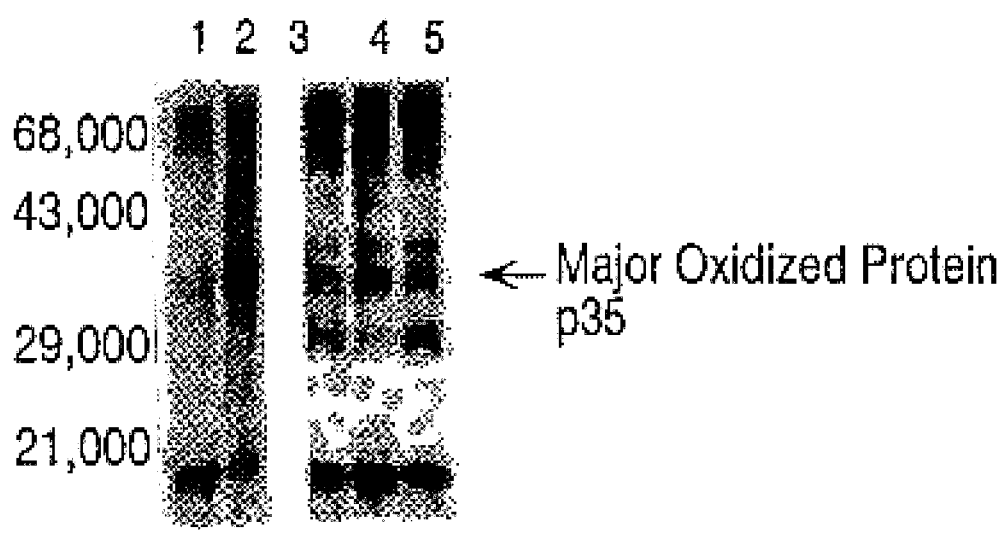
FIG. 10 shows a Western analysis of oxidized proteins in immune-activated PMBCs and Jurkat T cells transfected with the MnSOD E3(−) recombinant DNA, pBI-G/MnSOD E3(−).

As shown in FIG. 10, the protein, p35, is specifically oxidized in Jurkat T cells upon induction of the MnSOD E3(−) cDNA. The same or a co-migrating p35 is also oxidized in PMBCs shortly after influenza vaccination. This result shows that the MnSOD E3(−) isoform is associated with oxidative stress in cells, and the oxidation of p35 in activated PMBCs correlates well with the known expression of the MnSOD E3(−) mRNA splice variant.

Detection of Oxidized Total Cellular Proteins Containing Carbonyl Groups

Cellular extracts from PMBCs were analyzed by SDS-PAGE using the Oncor Oxyblot kit (Oncor) as described by Keller et al., Immunochemical detection of oxidized proteins, Chem Res Toxicol (1993) 6(4):430–33, incorporated herein by reference. To ensure that the antibody specifically detected carbonyl groups, a derivation control was included in which no 2,4-dinitrophenyl hydrazine was added to the extracts.

SEQUENCE LISTING

```
<160> NUMBER OF SEQ ID NOS: 14

<210> SEQ ID NO 1
<211> LENGTH: 552
<212> TYPE: DNA
<213> ORGANISM: Homo sapiens
<220> FEATURE:
<221> NAME/KEY: CDS
<222> LOCATION: (1)..(552)
<223> OTHER INFORMATION: Isoform of MnSOD E3(-)

<400> SEQUENCE: 1 atg ttg agc cgg gca gtg tgc ggc acc agc agg cag ctg cct ccg gtt    48
Met Leu Ser Arg Ala Val Cys Gly Thr Ser Arg Gln Leu Pro Pro Val
 1               5                  10                  15 ttg ggg tat ctg ggc tcc agg cag aag cac agc ctc ccc gac ctg ccc    96
Leu Gly Tyr Leu Gly Ser Arg Gln Lys His Ser Leu Pro Asp Leu Pro
             20                  25                  30 tac gac tac ggc gcc ctg gaa cct cac atc aac gcg cag atc atg cag   144
Tyr Asp Tyr Gly Ala Leu Glu Pro His Ile Asn Ala Gln Ile Met Gln
         35                  40                  45 ctg cac cac agc aag cac cac gcg gcc tac gtg aac aac ctg aac gtc   192
Leu His His Ser Lys His His Ala Ala Tyr Val Asn Asn Leu Asn Val
     50                  55                  60 acc gac gag aag tac cag gag gcg ttg gcc aag ggg gag ttg ctg gaa   240
Thr Asp Glu Lys Tyr Gln Glu Ala Leu Ala Lys Gly Glu Leu Leu Glu
 65                  70                  75                  80 gcc atc aaa cgt gac ttt ggt tcc ttt gac aag ttt aag gag aag ctg   288
Ala Ile Lys Arg Asp Phe Gly Ser Phe Asp Lys Phe Lys Glu Lys Leu
                 85                  90                  95 acg gct gca tct gtt ggt gtc caa ggc tca ggt tgg ggt tgg ctt ggt   336
Thr Ala Ala Ser Val Gly Val Gln Gly Ser Gly Trp Gly Trp Leu Gly
             100                 105                 110 ttc aat aag gaa cgg gga cac tta caa att gct gct tgt cca aat cag   384
Phe Asn Lys Glu Arg Gly His Leu Gln Ile Ala Ala Cys Pro Asn Gln
         115                 120                 125 gat cca ctg caa gga aca aca ggc ctt att cca ctg ctg ggg att gat   432
Asp Pro Leu Gln Gly Thr Thr Gly Leu Ile Pro Leu Leu Gly Ile Asp
     130                 135                 140 gtg tgg gag cac gct tac tac ctt cag tat aaa aat gtc agg cct gat   480
Val Trp Glu His Ala Tyr Tyr Leu Gln Tyr Lys Asn Val Arg Pro Asp
145                 150                 155                 160 tat cta aaa gct att tgg aat gta atc aac tgg gag aat gta act gaa   528
Tyr Leu Lys Ala Ile Trp Asn Val Ile Asn Trp Glu Asn Val Thr Glu
                165                 170                 175 aga tac atg gct tgc aaa aag taa                                    552
Arg Tyr Met Ala Cys Lys Lys
            180

<210> SEQ ID NO 2
<211> LENGTH: 183
<212> TYPE: PRT
<213> ORGANISM: Homo sapiens
```

<400> SEQUENCE: 2

```
Met Leu Ser Arg Ala Val Cys Gly Thr Ser Arg Gln Leu Pro Pro Val
  1               5                  10                  15
Leu Gly Tyr Leu Gly Ser Arg Gln Lys His Ser Leu Pro Asp Leu Pro
             20                  25                  30
Tyr Asp Tyr Gly Ala Leu Glu Pro His Ile Asn Ala Gln Ile Met Gln
         35                  40                  45
Leu His His Ser Lys His His Ala Ala Tyr Val Asn Asn Leu Asn Val
     50                  55                  60
Thr Asp Glu Lys Tyr Gln Glu Ala Leu Ala Lys Gly Glu Leu Leu Glu
 65                  70                  75                  80
Ala Ile Lys Arg Asp Phe Gly Ser Phe Asp Lys Phe Lys Glu Lys Leu
                 85                  90                  95
Thr Ala Ala Ser Val Gly Val Gln Gly Ser Gly Trp Gly Trp Leu Gly
            100                 105                 110
Phe Asn Lys Glu Arg Gly His Leu Gln Ile Ala Ala Cys Pro Asn Gln
        115                 120                 125
Asp Pro Leu Gln Gly Thr Thr Gly Leu Ile Pro Leu Leu Gly Ile Asp
    130                 135                 140
Val Trp Glu His Ala Tyr Tyr Leu Gln Tyr Lys Asn Val Arg Pro Asp
145                 150                 155                 160
Tyr Leu Lys Ala Ile Trp Asn Val Ile Asn Trp Glu Asn Val Thr Glu
                165                 170                 175
Arg Tyr Met Ala Cys Lys Lys
                180
```

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: probe, exon 2-exon 4 junction

<400> SEQUENCE: 3
taccaggagg cgttggccaa gggggagttg ctggaagcca tcaaa    45

<210> SEQ ID NO 4
<211> LENGTH: 12
<212> TYPE: PRT
<213> ORGANISM: Homo sapiens

<400> SEQUENCE: 4

```
Gln Glu Ala Leu Ala Lys Gly Glu Leu Leu Glu Ala
  1               5                  10
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: PCR primer, exon 1 forward

<400> SEQUENCE: 5
agccagctct agaagcatgt tgag    24

<210> SEQ ID NO 6
<211> LENGTH: 25

```
<212> TYPE: DNA
<213> ORGANISM: Artificial Sequence
<220> FEATURE:
<223> OTHER INFORMATION: Description of Artificial Sequence: PCR
      primer, exon 5 reverse

<400> SEQUENCE: 6
attctgcagt actctagacc actac                                              25

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: PCR
      primer, exon 2 forward

<400> SEQUENCE: 7
gctctagaac ctcacatcaa c                                                  21

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: PCR
      primer, exon 4 reverse

<400> SEQUENCE: 8
tttctagagc cttggacacc aacag                                              25

<210> SEQ ID NO 9
<211> LENGTH: 6
<212> TYPE: PRT
<213> ORGANISM: Homo sapiens
<220> FEATURE:
<223> OTHER INFORMATION: amino acid sequence at exon 2-exon 4 junction

<400> SEQUENCE: 9

Leu Ala Lys Gly Glu Leu
 1               5

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: RT-PCR
      primer, 1F

<400> SEQUENCE: 10
agccagctct agaagcatgt tgag                                               24

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: RT-PCR
      primer, 710R

<400> SEQUENCE: 11
attctgcagt actctagacc actac                                              25

<210> SEQ ID NO 12
<211> LENGTH: 18
<212> TYPE: DNA
<213> ORGANISM: Homo sapiens
```

```
<220> FEATURE:
<221> NAME/KEY: misc_feature
<223> OTHER INFORMATION: intron between exons 2 and 3 of MnSOD gene

<400> SEQUENCE: 12
tggccaaggg agatgtta                                                        18

<210> SEQ ID NO 13
<211> LENGTH: 18
<212> TYPE: DNA
<213> ORGANISM: Homo sapiens
<220> FEATURE:
<221> NAME/KEY: misc_feature
<223> OTHER INFORMATION: intron between exons 3 and 4 of MnSOD gene

<400> SEQUENCE: 13
aacccaaagg ggagttgc                                                        18

<210> SEQ ID NO 14
<211> LENGTH: 37
<212> TYPE: DNA
<213> ORGANISM: Homo sapiens
<220> FEATURE:
<221> NAME/KEY: misc_feature
<223> OTHER INFORMATION: intron between exons 2 and 4 of MnSOD gene
      (splice variant)

<400> SEQUENCE: 14
tggccaaggg ggagttgctg gaagccatca aacgtga                                   37
```

What is claimed:

1. An isolated polypeptide comprising the amino acid sequence of SEQ ID NO: 4.

2. The isolated polypeptide of claim 1, wherein the polypeptide is an exon 3-deleted isoform of MnSOD.

3. The isolated polypeptide of claim 1, wherein the amino acid sequence comprises SEQ ID NO: 2.

4. The isolated polypeptide of claim 3, wherein the amino acid sequence is encoded by a nucleic acid sequence comprising SEQ ID NO: 1.

5. An isolated polypeptide consisting of the amino acid sequence of SEQ ID NO: 4.

6. An isolated polypeptide consisting of the amino acid sequence of SEQ ID NO: 2.

7. The isolated polypeptide of claim 1, wherein the polypeptide is selected from the group consisting of (a) an isolated polypeptide comprising a fragment of a polypeptide comprising the amino acid sequence of SEQ ID NO: 2, (b) an isolated polypeptide comprising conservative amino acid substitutions of the amino acid sequence of SEQ ID NO: 2; and (c) an isolated polypeptide wherein one or more of the amino acid residues includes a substituent group;

wherein the polypeptide has a pro-oxidant effect.

8. The isolated polypeptide of claim 7, wherein the activity of the polypeptide is nonspecific oxidative damage to mtDNA.

9. The isolated polypeptide of claim 1, wherein the polypeptide is fused to a second polypeptide.

10. The isolated polypeptide of claim 9, wherein the second polypeptide is a hexa-His tag.

11. The isolated polypeptide of claim 9, wherein the second polypeptide is a hemagglutin tag.

* * * * *